US008469700B2

(12) United States Patent
Peluso et al.

(10) Patent No.: US 8,469,700 B2
(45) Date of Patent: Jun. 25, 2013

(54) FOULING AND CORROSION DETECTOR FOR BURNER TIPS IN FIRED EQUIPMENT

(75) Inventors: Marcos Peluso, Chanhassen, MN (US); Scott Eliason, Chaska, MN (US); Gregory C. Brown, Chanhassen, MN (US)

(73) Assignee: Rosemount Inc., Eden Prairie, MN (US)

( * ) Notice: Subject to any disclaimer, the term of this patent is extended or adjusted under 35 U.S.C. 154(b) by 1146 days.

(21) Appl. No.: 11/238,658

(22) Filed: Sep. 29, 2005

(65) Prior Publication Data
US 2007/0072137 A1    Mar. 29, 2007

(51) Int. Cl.
G01N 29/036 (2006.01)
F23D 14/24 (2006.01)

(52) U.S. Cl.
USPC ............. 431/13; 431/77; 431/183; 431/187; 73/590; 73/117.3; 73/579

(58) Field of Classification Search
USPC ............... 431/183, 187, 188, 353; 73/117.3, 73/19.05, 199 A
See application file for complete search history.

(56) References Cited

U.S. PATENT DOCUMENTS

| | | | |
|---|---|---|---|
| 2,840,146 A | 6/1958 | Ray | 158/28 |
| 2,844,730 A | 7/1958 | Tandler et al. | 250/43.5 |
| 3,185,845 A | 5/1965 | Lively et al. | 250/83.6 |
| 3,301,307 A | 1/1967 | Nishigaki et al. | 431/78 |
| 3,416,041 A | 12/1968 | Giuffrida et al. | 317/148.5 |
| 3,504,490 A | 4/1970 | Klamm | 60/39.09 |
| 3,506,830 A | 4/1970 | Love, III et al. | 250/83.3 |
| 3,583,844 A | 6/1971 | Smith | 431/79 |
| 3,611,805 A | 10/1971 | Hishikari | 73/355 |
| 3,689,773 A | 9/1972 | Wheeler | 431/79 |
| 3,825,913 A | 7/1974 | Metcalf et al. | 431/79 |
| 3,859,520 A | 1/1975 | Hertzberg et al. | 250/209 |
| 3,886,351 A | 5/1975 | Williams | 250/206 |
| 3,965,360 A | 6/1976 | Sakasegawa et al. | 250/461 |
| 3,970,430 A | 7/1976 | Reader, Jr. et al. | 23/232 |
| 3,995,221 A | 11/1976 | MacDonald | 328/6 |
| 4,016,424 A | 4/1977 | Traina | 250/372 |
| 4,029,966 A | 6/1977 | Baker et al. | 250/372 |

(Continued)

FOREIGN PATENT DOCUMENTS

| | | |
|---|---|---|
| EP | 0 638 770 | 2/1995 |
| EP | 0 816 760 | 1/1998 |

(Continued)

OTHER PUBLICATIONS

Office Action from corresponding European Application No. 06814910.3, dated Mar. 24, 2009.

(Continued)

*Primary Examiner* — Steven B McAllister
*Assistant Examiner* — Nikhil Mashruwala
(74) *Attorney, Agent, or Firm* — Westman, Champlin & Kelly, P.A.

(57) ABSTRACT

A system for predicting fouling and corrosion of a combustion system in an industrial process includes a pipe, a restrictive element, and a fouling and corrosion detector. The pipe contains a fuel. The restrictive element is coupled to the pipe and the fuel passes through the restrictive element. The fouling and corrosion detector is coupled to the pipe and is adapted to detect a characteristic signature of the restrictive element and to generate an alarm if a change in the detected signature exceeds a predetermined limit relative to a baseline signature.

9 Claims, 5 Drawing Sheets

U.S. PATENT DOCUMENTS

| | | | | |
|---|---|---|---|---|
| 4,045,679 A | 8/1977 | Wolfe et al. | | 250/461 |
| 4,051,375 A | 9/1977 | Schuetz et al. | | 250/372 |
| 4,065,672 A | 12/1977 | Harpster | | 250/372 |
| 4,220,857 A | 9/1980 | Bright | | 250/339 |
| 4,233,596 A | 11/1980 | Okamoto et al. | | 340/578 |
| 4,280,058 A | 7/1981 | Tar | | 250/554 |
| 4,326,798 A | 4/1982 | Kahn | | 356/45 |
| 4,369,748 A | 1/1983 | Steinke et al. | | 123/425 |
| 4,370,557 A | 1/1983 | Axmark et al. | | 250/554 |
| 4,397,283 A | 8/1983 | Komaroff et al. | | 123/494 |
| 4,419,212 A | 12/1983 | Dietz et al. | | 204/424 |
| 4,455,487 A | 6/1984 | Wendt | | 250/339 |
| 4,541,272 A | 9/1985 | Bause | | 73/118 |
| 4,553,031 A | 11/1985 | Cholin et al. | | 250/339 |
| 4,561,786 A | 12/1985 | Anderson | | 374/129 |
| 4,578,583 A | 3/1986 | Ciammaichella et al. | | 250/339 |
| 4,594,968 A | 6/1986 | Degobert et al. | | 123/1 |
| 4,599,568 A | 7/1986 | Couch | | 328/6 |
| 4,616,137 A | 10/1986 | Goff et al. | | 250/554 |
| 4,632,563 A | 12/1986 | Lord, III | | 356/437 |
| 4,639,717 A | 1/1987 | De Meirsman | | 340/578 |
| 4,691,196 A | 9/1987 | Kern et al. | | 340/578 |
| 4,694,172 A | 9/1987 | Powell et al. | | 250/339 |
| 4,701,624 A | 10/1987 | Kern et al. | | 340/578 |
| 4,706,629 A | 11/1987 | Wineland et al. | | 123/478 |
| 4,706,630 A | 11/1987 | Wineland et al. | | 123/478 |
| 4,709,155 A | 11/1987 | Yamaguchi et al. | | 250/554 |
| 4,730,925 A | 3/1988 | Chiba et al. | | 356/311 |
| 4,742,236 A | 5/1988 | Kawakami et al. | | 250/554 |
| 4,770,129 A | 9/1988 | Miyata et al. | | 123/1 |
| 4,785,292 A | 11/1988 | Kern et al. | | 340/578 |
| 4,795,256 A | 1/1989 | Krause et al. | | 356/320 |
| 4,799,787 A | 1/1989 | Mason | | 356/43 |
| 4,815,841 A | 3/1989 | Bickler et al. | | 356/43 |
| 4,818,705 A | 4/1989 | Schneider et al. | | 436/164 |
| 4,822,564 A | 4/1989 | Howard | | 422/52 |
| 4,887,574 A | 12/1989 | Kuroiwa et al. | | 123/425 |
| 4,919,099 A | 4/1990 | Extance et al. | | 123/425 |
| 4,930,478 A | 6/1990 | Plee et al. | | 123/425 |
| 4,940,033 A | 7/1990 | Plee et al. | | 123/425 |
| 4,959,638 A * | 9/1990 | Palmer | | 340/577 |
| 4,974,552 A | 12/1990 | Sickafus | | 123/1 |
| 4,983,853 A | 1/1991 | Davall et al. | | 250/554 |
| 4,996,427 A | 2/1991 | Noble et al. | | 250/332 |
| 5,024,055 A | 6/1991 | Sato et al. | | 60/39.27 |
| 5,031,234 A | 7/1991 | Primas et al. | | 455/605 |
| 5,039,189 A | 8/1991 | Lytel et al. | | 385/2 |
| 5,040,242 A | 8/1991 | Tsuchiya et al. | | 359/154 |
| 5,049,063 A | 9/1991 | Kishida et al. | | 431/79 |
| 5,060,302 A | 10/1991 | Grimes | | 359/135 |
| 5,067,463 A | 11/1991 | Remboski et al. | | 123/425 |
| 5,073,104 A | 12/1991 | Kemlo | | 431/12 |
| 5,111,333 A | 5/1992 | Coles et al. | | 359/333 |
| 5,111,519 A | 5/1992 | Mathis | | 385/24 |
| 5,113,828 A | 5/1992 | Remboski et al. | | 123/425 |
| 5,125,381 A | 6/1992 | Nutton et al. | | 123/425 |
| 5,136,666 A | 8/1992 | Anderson et al. | | 385/24 |
| 5,148,667 A | 9/1992 | Morey | | 60/39.02 |
| 5,155,545 A | 10/1992 | Rinke | | 356/300 |
| 5,162,658 A | 11/1992 | Turner et al. | | 340/578 |
| 5,186,146 A | 2/1993 | Sohma et al. | | 123/435 |
| 5,210,702 A | 5/1993 | Bishop et al. | | 364/496 |
| 5,225,810 A | 7/1993 | Inoue et al. | | 340/577 |
| 5,236,328 A | 8/1993 | Tate et al. | | 431/79 |
| 5,241,367 A | 8/1993 | Grob et al. | | 356/435 |
| 5,257,496 A | 11/1993 | Brown et al. | | 60/39.06 |
| 5,263,851 A | 11/1993 | Hosome et al. | | 431/79 |
| 5,303,684 A | 4/1994 | Brown et al. | | 123/425 |
| 5,317,165 A | 5/1994 | Montagna | | 340/578 |
| 5,495,112 A | 2/1996 | Maloney et al. | | 431/79 |
| 5,548,277 A | 8/1996 | Wild | | 431/78 |
| 5,565,672 A | 10/1996 | Siegel et al. | | 250/214 |
| 5,612,676 A | 3/1997 | Plimpton et al. | | 340/578 |
| 5,646,573 A | 7/1997 | Bayruns et al. | | 250/214 |
| 5,650,943 A | 7/1997 | Powell et al. | | 364/550 |
| 5,665,916 A | 9/1997 | Puster et al. | | 73/590 |
| 5,748,090 A | 5/1998 | Borg et al. | | 340/578 |
| 5,828,797 A | 10/1998 | Minott et al. | | 385/12 |
| 5,853,022 A | 12/1998 | Eggleston et al. | | 137/270 |
| 5,961,314 A | 10/1999 | Myhre et al. | | 431/79 |
| 6,013,919 A | 1/2000 | Schneider et al. | | 250/554 |
| 6,238,622 B1 | 5/2001 | Salimian | | 422/54 |
| 6,490,927 B2 * | 12/2002 | Braunling et al. | | 73/597 |
| 6,700,496 B2 | 3/2004 | Francke et al. | | 340/578 |
| 6,710,345 B2 | 3/2004 | Carter et al. | | 250/338.5 |
| 6,713,733 B2 | 3/2004 | Kochman et al. | | 219/549 |
| 7,290,450 B2 * | 11/2007 | Brown et al. | | 73/579 |
| 7,950,919 B2 | 5/2011 | Johnson et al. | | 431/12 |
| 2002/0067255 A1 | 6/2002 | Tanizawa | | 340/514 |
| 2003/0183537 A1 | 10/2003 | Eden et al. | | 205/775.5 |
| 2004/0036020 A1 | 2/2004 | Sakairi et al. | | 250/288 |
| 2005/0234673 A1 * | 10/2005 | Saitoh et al. | | 702/114 |

FOREIGN PATENT DOCUMENTS

| | | |
|---|---|---|
| FR | 2 274 869 | 6/1974 |
| GB | 2 178 841 | 2/1987 |
| GB | 2 393 514 A | 3/2004 |
| JP | 56 092326 | 7/1981 |
| JP | 58 033025 | 2/1983 |
| JP | 61-197726 | 2/1985 |
| JP | 60-164120 | 8/1985 |
| JP | 62-158922 | 7/1987 |
| JP | 4143515 | 5/1992 |
| JP | 59-109715 | 6/1994 |
| JP | 6254377 | 9/1994 |
| JP | 2004077292 | 3/2004 |
| JP | 2005091332 | 4/2005 |
| SU | 1455-150 | 1/1989 |

OTHER PUBLICATIONS

"Lean Blowout detection in a Single Nozzle Swirl Cup Combustor" by S. Nair et al., $42^{ND}$ AIAA Aerospace Sciences Meeting and Exhibit, Jan. 2004, pp. 1-12.

"Acoustic Detection of Imminent Blowout in Pilot and Swirl Stabilized Combustors" by S. Nair et al., Proceedings of ASME/IGTI Turbo Expo 2003, pp. 1-10.

"Notification of Transmittal of the International Search Report and the Written Opinion of the International Searching Authority" for PCT/US2006/036399.

"Acoustic Temperature Measurement of Combustion Chambers", by JL Munoz et al pp. 5/1-5/4, 2000.

"Acoustic Control of Combustion Instabilities and Emission in a Gas-Turbine Combustor", by C. Paschereit et al., Proceedings of the 1998 IEEE Internatio Conference on Control Applications, pp. 1175-1179, Sep. 1998.

"Advanced Monitoring and Characterisation of Combustion Flames" by G. Lu et al., pp. 3/1-3/4, 2000.

"Air-Coupled Ultrasonic Tomographic Imaging of High-Temperature Flames", by T. Gan et al., IEEE Transactions on Ultrasonics, Ferroelectrics, and Frequency Control, vol. 50, No. 9, pp. 1214-1218, Sep. 2003.

"Instabilities in the Near Wake of a Rod with an Anchored Flame", by J. Quinard, IEEE, pp. 60-67, 1991.

Office Action from corresponding Russian Application No. 2008116843/06(019215), dated Jun. 21, 2010.

Office Action from corresponding Russian Application No. 2008116843/06(019215), dated Oct. 18, 2010, 6 pages.

Notification of Reasons for Rejection from corresponding Japanese Application No. 2008-533431, dated Nov. 8, 2010, 9 pages.

First Office Action from related Chinese application No. 200680035852.8, facsimile date Feb. 25, 2011, 4 pages.

Decision on Grant from related Russian application No. 2008116843/06 (019215), date Feb. 3, 2010, 11 pages. Translation and official Russian document.

Office Action from related Japanese application No. 2008-533431,dated Jul. 12, 2011, 9 pages.

Second Office Action from related Chinese application No. 200680035852.8, facsimile date Feb. 23, 2012.

* cited by examiner

FOULING AND CORROSION DETECTOR FOR BURNER TIPS IN FIRED EQUIPMENT

BACKGROUND OF THE INVENTION

The present invention relate to combustion systems. More particularly, the invention relates to an apparatus for detecting fouling or corrosion in burner tips within a fired equipment system.

The term "fired equipment" or "heat delivery system" refers to devices that utilize fire or flames to deliver heat to a system. Typically, fired equipment utilizes a fuel delivery system for controlled delivery of fuel to a combustion chamber or to a burner tip. As used herein, the term "fuel" may be a gas, a liquid, a flammable mixture (such as coal particles in an oil suspension), or any flammable substance that is amenable to controlled delivery through a burner tip. Examples of fired equipment include incinerators, heat exchangers, reactors, boilers, and the like. One common failure mode for processes that use fired equipment is fouling or corrosion of the burner tips or nozzles, which deliver fuel to the combustion chamber. Such fouling or corrosion can impact fuel delivery, and can result in system failure and sometimes plant shut down.

In the process industry, unplanned plant downtime events caused by fired equipment failure can be very expensive, including lost production costs and the cost of shutdown/start up. In addition to such costs, the events that caused the plant downtime can also result in safety issues, environmental issues, and faulty products. Devices to provide diagnostic information and to generate alarms are used in process control industries to avoid such unplanned events when possible.

One diagnostic technique involves the use of process variables (PVs), which are monitored, and if determined limits are exceeded, an alarm condition is reported. Such an alarm is really just a detection of a symptom of the failure. The actual cause of the failure is left to be determined or inferred from other process information available to the control room, or available at the instrument generating the alarm. While sometimes the instrument itself may be at fault, such a situation is becoming less likely as instrumentation achieves higher and higher reliability. Usually, an alarm event is generated based on an aspect in the process itself going bad.

Conventionally, burner tip fouling or plugging was detected by noting a low fuel flow to the fired device, or by inference based on the inability to achieve the desired target process temperature. In some embodiments, a fired equipment unit has multiple burner tips, making upstream detection somewhat difficult. Specifically, as a single burner tip within a set of burner tips becomes plugged or corroded, an upstream sensor may not detect any change in fuel flow to the burner unit having multiple burner tips, because some burner tips of the burner unit may simply produce a slightly larger flame. Alternatively, if the fuel is corrosive, a corroded burner tip may simply burn more fuel but less efficiently. Identifying which burner tip is actually plugged or corroded may be difficult if not impossible without shutting down the system.

Another problem associated with such systems is that fouling and/or corrosion of a burner tip typically causes lower heat output. Compensation for such lower heat output may include increasing fuel flow to the system. The increased fuel flow may result in increased flame output from other, unplugged burners, thereby creating an uneven heating situation or hot spots within the system. Uneven heating may result in decreased efficiency, decreased product quality, and various other undesirable results. Moreover, if the burners are burn more fuel because another burner is plugged, they may produce a flame that is hotter than that for which the burner is rated, thereby exposing the burner to a temperature greater than it can withstand. Such hot spots eventually can lead to premature failure of the tubes or separator walls. Within the process itself, such hot spots may ruin the process.

There is an ongoing need in the art for a fouling and corrosion detection system for predicting when a burner tip or other flow obstruction elements are becoming fouled or corroded, so that the system can be serviced. Embodiments of the present invention provide solutions to these and other problems, and provide other advantages over the prior art.

SUMMARY

A system for predicting fouling and corrosion of a combustion system in an industrial process includes a pipe, a restrictive element, and a fouling and corrosion detector. The pipe contains a fuel. The restrictive element is coupled to the pipe and the fuel passes through the restrictive element. The fouling and corrosion detector is coupled to the pipe and is adapted to detect a characteristic signature of the restrictive element and to generate an alarm if a change in the detected signature exceeds a predetermined limit relative to a baseline signature.

DETAILED DESCRIPTION

Generally, fluids flowing within a pipe or conduit produce detectable acoustic signals as the fluid contacts the walls of the pipe. Adjacent to narrowing or obstructive elements within a pipe (such as a venture tube, a burner tip, and the like), the changing inner diameter of the pipe cause acoustic reflections, which are detectable upstream from the narrowing or obstructive element. For example, as fuel flows through a burner tip, the fuel flow through the narrowing flow path causes an acoustic reflection substantially opposite to the direction of flow. Typically, this acoustic reflection can be considered as an acoustic signature, which varies with flow rate. However, this acoustic reflection or signature changes as fouling or corrosion effects the narrowing or obstructing element. Both fouling (buildup of undesirable material on the surface) or corrosion (pitting or erosion of surface material) cause a change in the profile of the obstructing or narrowing element, resulting in a change in the acoustic signature indicative of fouling or corrosion. By detecting acoustic signature change that exceeds a predetermined limit, the system can be monitored for fouling or corrosion and serviced before the system fails.

In some instances, process noise falls largely within a band of frequencies which can make detection of the reflected signal difficult. In such instances, the present invention continues to make use of the existing flow obstruction by reflecting an acoustic signal in a different frequency band off of the obstruction and measuring the reflected acoustic signature to detect a change exceeding the predetermined limit. Specifically, an acoustic broad-band signal directed through the gas tube toward the burner tip produces an acoustic reflection from the burner tip, which changes as the burner tip becomes corroded or fouled.

In addition to a change in acoustic signature, fouling or corrosion of the burner tip alter the optical signature of the burner tip and of the flame itself. Depending on the fuel/air mixture and on the presence of contaminants, the heat signature, color, flame profile, torch shape and so on may vary. Moreover, plugging or corrosion of the burner tip may impact burner tip efficiency, causing the burner tip to become hotter than normal or to experience uneven heating. While the system variables are held constant, a flame of a burner tip maintains relatively a constant shape, size, heat signature, and so on. If impurities are introduced to the flame, colors associated with the chemical composition of the introduced material may also, appear in the flame. If the burner tip becomes corroded or fouled, the flame may oscillate and the flame shape may vary. Moreover, the heat signature of the flame may begin to include cold areas that are not present in a flame produced by a clean burner tip. These variations can be detected using various optical sensing means, which are discussed in greater detail below.

Figure 1:
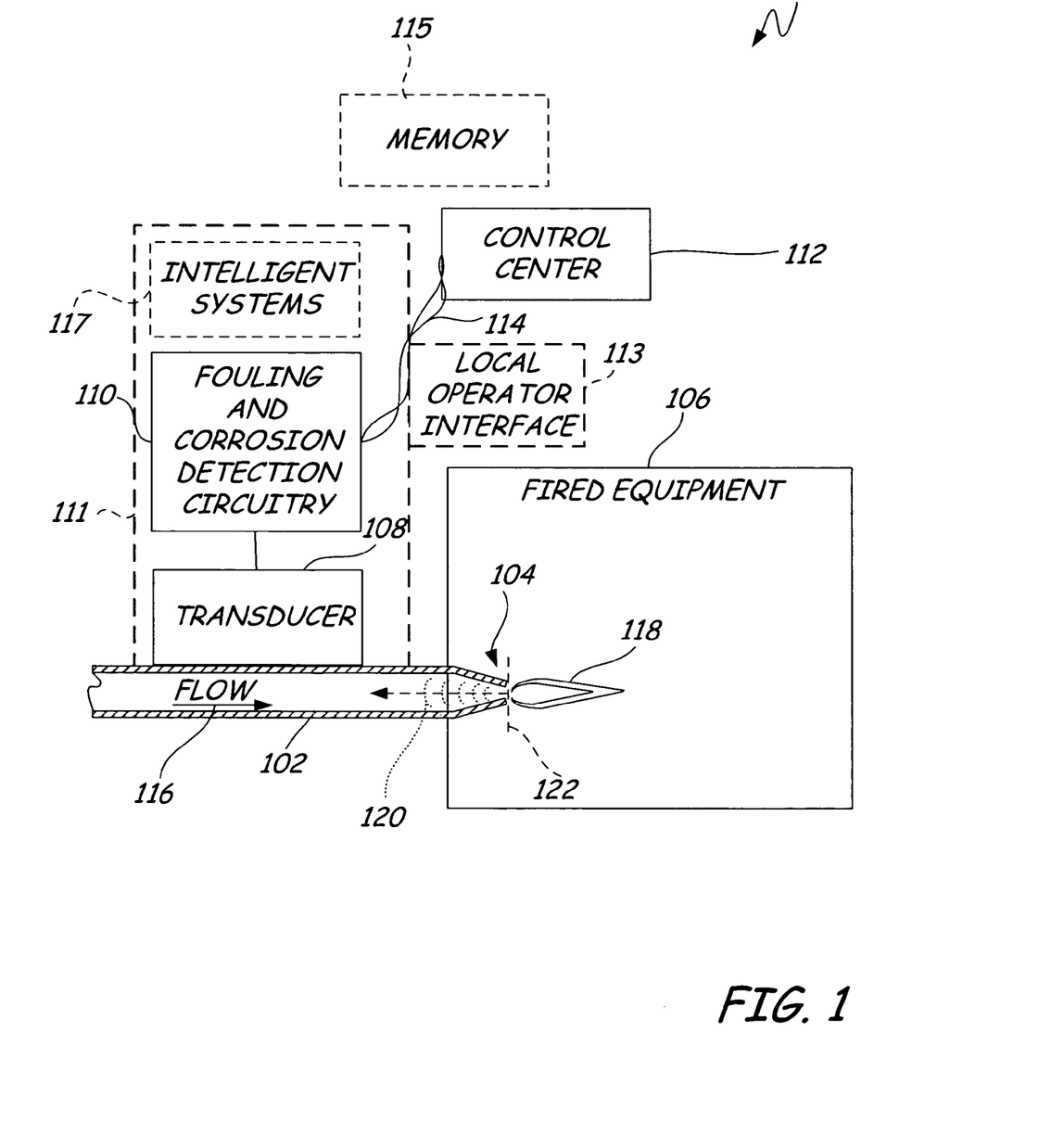
FIG. 1 is a simplified diagram of a burner tip fouling and corrosion detector system according to an embodiment of the present invention.

FIG. 1 illustrates a simplified diagram of a fouling and corrosion detection system 100 in accordance with an embodiment of the present invention. The system 100 includes a flow pipe 102 with a burner tip 104 (which presents a narrowing internal diameter relative to the flow pipe 102). The burner tip 104 extends into the fired equipment 106 to deliver heat via flame 118. Fired equipment 106 may be a boiler or any other type of equipment in an industrial process for which flame heat is required.

A transducer 108 is coupled to the flow pipe 102 upstream from the burner tip 104. The transducer 108 is coupled to fouling and corrosion detection circuitry 110, which is in turn coupled to control center 112 via communications link 114. The communications link 114 may be a wired or wireless communications link. Additionally, communications link 114 may be a two, three, or four wire loop including power and ground wires. The fouling and corrosion circuitry 110 and the control center 112 communicate over the communications link 114, providing measurement information and control signals, respectively.

Memory 115 is provided to store measurement information, so that current measurements taken by the transducer 108 can be compared with baseline measurements to identify changes indicative of fouling or corrosion. Memory 115 is shown in phantom because the memory 115 may be located in any number of locations, such as within a transmitter housing 111 along with the transducer 108 and the fouling and corrosion detection circuitry 110. Alternatively, the memory 115 may be maintained in the control center 112. In a preferred embodiment, the memory 115 stores a baseline (non-fouled or non-corroded) acoustic signature of the narrowing element (such as burner tip 104). In one embodiment, the measurement information is stored as raw data, meaning that the measurement count or voltage information is stored, as opposed to conditioned process variable information. In an alternative embodiment, the processed measurement data is stored. A local operator interface 113 may be provided to allow a local operator or user to configure the initial conditions (such as by resetting a baseline signature measurement after a new burner tip 104 is installed or after the plugged tip has been serviced).

Optionally, intelligent systems 117 may be utilized to improve the accuracy of the system. Intelligent systems 117 may include self-learning systems, neural networks, fuzzy logic, artificial intelligence, and the like.

As fuel flows toward the burner tip 104, as indicated by arrow 116, the fuel is forced into the narrowing inner diameter of the burner tip 104. An acoustic reflection (indicated by reference numeral 120) is generated by the fuel flowing through the narrowing passageway. This acoustic reflection 120 is measured by the transducer 108. Generally, the acoustic reflection 120 is generated by the narrowing burner tip 104, and does not generally result from noise from the flame 118. A dotted line 122 illustrates the general cut off line where the reflected noise signal 120 may originate.

Generally, at installation or during servicing, a baseline measurement is recorded by the transducer 108 and stored in memory 115. During use, the acoustic reflection 120 of the burner tip 104 is monitored and measurements taken by the transducer 108 are compared against the stored baseline measurement by the fouling and corrosion detection circuitry 110. If the measured acoustic reflection 120 exceeds a predetermined limit as compared with the stored baseline signature, the fouling and corrosion detection circuitry 110 is adapted to generate an alarm signal to the control center 112.

It is also possible to detect "flame out" conditions using the transducer 108. Specifically, if the burner tip 104 becomes completely plugged, the reflected noise signature will disappear (or change dramatically, such that the measurement data will change like a voltage step). If the burner tip 104 is not plugged but the gas is shut off (meaning there is no fuel flow to the tip 104), the pressure transducer 108 will indicate near zero pressure. Thus, the device can differentiate between a shut off fuel supply and a plugged tip 104.

Generally, the transducer 108 may be a pressure transducer or an appropriate acoustic sensor. In either case, several transducers can be brought into a common electronics, such that a transducer can be associated with each burner tip 104. If acoustic sensors are utilized, it may be desirable to couple one or more additional pressure sensors to a burner assembly, to assist in differentiating between a burner off condition and a plugged or fouled burner tip.

For fired equipment that is operated over a wide range of fuel feed rates, a correlation between a feed rate and a burner tip back pressure (as measured by a pressure transducer) can be inferred. Storing reference noise signatures for various back pressure ranges provides a better predictive fouling detection capability. As the fuel feed rate changes, the reference noise signature appropriate for that back pressure range would be used for comparing with the present measured noise signature.

Various methods may be used to determine a noise signature for a narrowing element (such as burner tip 104). For example, a Fast Fourier Transform may be applied to the measurement data. In a preferred embodiment, wavelet technology is applied to the measurement data to decompose the measured waveform because it works well with signals having high noise content. The wavelet decomposition of a signal offers an advantage over the Fourier decomposition in that local or short-term contributions to the signal can be better represented.

In general, the present invention offers a number of advantages over prior art fouling and corrosion detection schemes. First, by positioning the transducer (acoustic detector or pressure sensor) upstream from the burner tip 104 (but adjacent to the burner tip), the transducer 108 does not encounter direct heating and can therefore avoid issues related to heat cycling and direct heat exposure. Secondly, the transducer 108 provides a sensitive, predictive method of determining burner tip fouling and corrosion. Thirdly, the transducer 108 may be implemented in a number of different ways. In a preferred embodiment, the transducer is integral to a transmitter. Another advantage is that information about the fuel flow rate is not required to provide information about fouling or plugging. Moreover, the present invention is capable of distinguishing between "fuel off" and plugged tip conditions. The transmitter 108 can also provide a fuel pressure PV as a side benefit. Finally, the present invention does not load the distributed control system any more than a normal transmitter PV. For most applications, a 4-20 mA loop power is sufficient to power the detector.

Figure 2A:
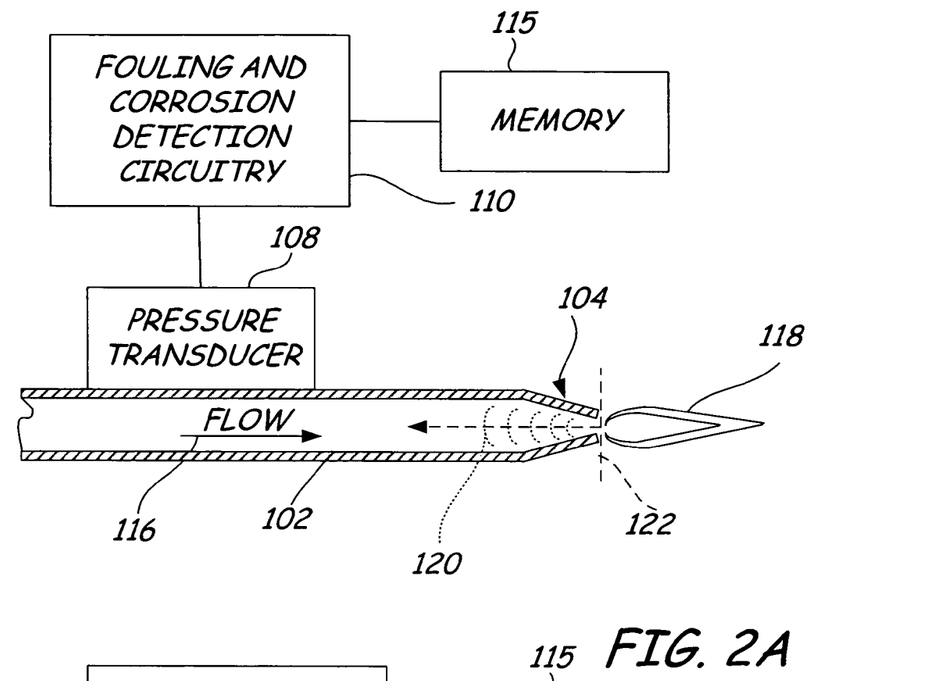
FIGS. 2A and 2B are simplified diagrams of a passive acoustic burner tip fouling and corrosion detector system according to an embodiment of the present invention.
Figure 2B:
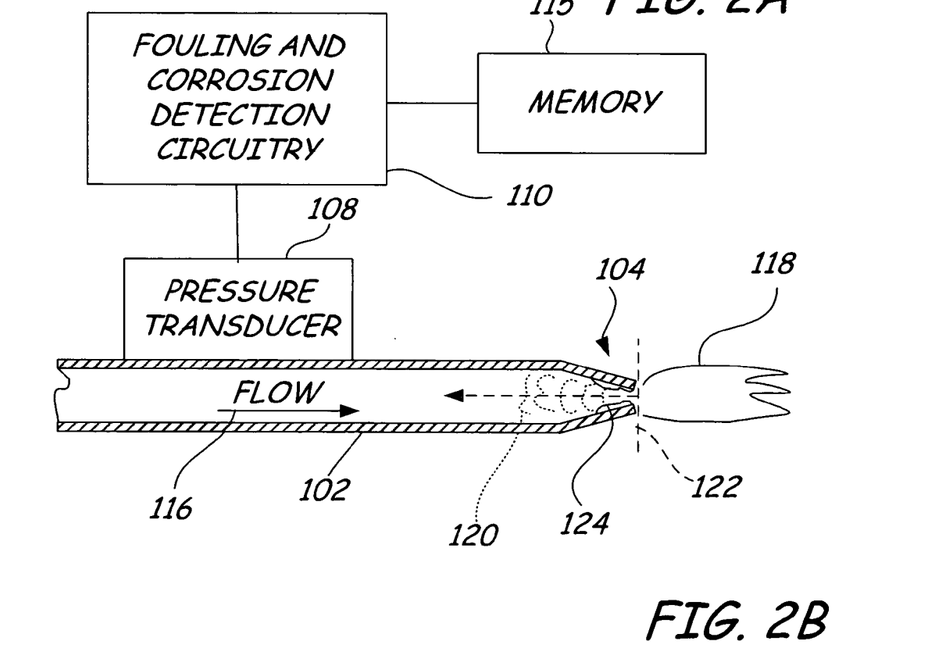

FIGS. 2A and 2B illustrate a simplified block diagram of a passive fouling and corrosion detector associated with a single burner tip according to an embodiment of the present invention. The fouling and corrosion detector has a fuel flow tube 102 with a burner tip 104, and a pressure transducer 108 coupled to the tube 102. Fluid or gas flow 116 passes through the tube 102 and through an opening in the burner tip 104, and a reflected noise signal 120 is reflected back to the pressure transducer 108, which detects the tip noise reflection 120. The measured reflected acoustic signal 120 is then processed by the fouling and corrosion detection circuitry 110, which compares the measured signal 120 against a baseline signal stored in memory 115. In FIG. 2A, the burner tip 104 is clean, so the comparison should result in no alarm signal.

FIG. 2B shows a detector associated with a burner tip 104 that is partially plugged or fouled by the deposits 124 (or alternatively corroded), resulting in an altered acoustic reflection 120 (as compared with the reflection shown in FIG. 2A). The transmitter 108 detects the changed reflected signal 120 indicating a fouled tip 104. The fouling and corrosion detection circuitry 110, which is coupled to the pressure transducer 108, then compares the measured reflection signal 120 against stored measurement data in the memory 115. If the difference between the stored signal and the measured signal 120 exceeds a predetermined limit, an alarm signal can be generated to the control center. In a preferred embodiment, a pressure transmitter with adequate bandwidth to sense the noise frequency of interest is utilized to obtain a burner tip flow acoustic or noise signature.

As used herein, the terms "acoustic" and "noise" refer to a compression-type pressure wave or other vibration having a frequency that may or may not fall within an audible frequency range. During installation or maintenance, a reference noise signature is measured and stored in a memory (either in the transmitter, at a control center, or even within the fouling and corrosion detection circuitry). Additional noise signatures are measured during normal burner tip operation and compared to the reference value. If the change in the noise signature is greater than a predetermined limit, an alarm or warning is provided on the device output signal.

In general, the device electronics provide the capability of having initial values set via an external device, via the control center, or a via local, integral operator interface. In a preferred embodiment, the electronics support bi-directional communication via a digital bus such as HART®, Foundation FieldBus, CAN, or other communication protocols. In general, this communication capability can be utilized to set initial values and to output various levels of alarm criticality, as well as potentially a PV in the case of a transmitter base device. In addition, acoustic sensor health can be reported via a digital bus. For a transmitter, the electronics are typically 4-20 mA loop powered; however, other electronics and other communication techniques may be utilized.

Figure 3A:
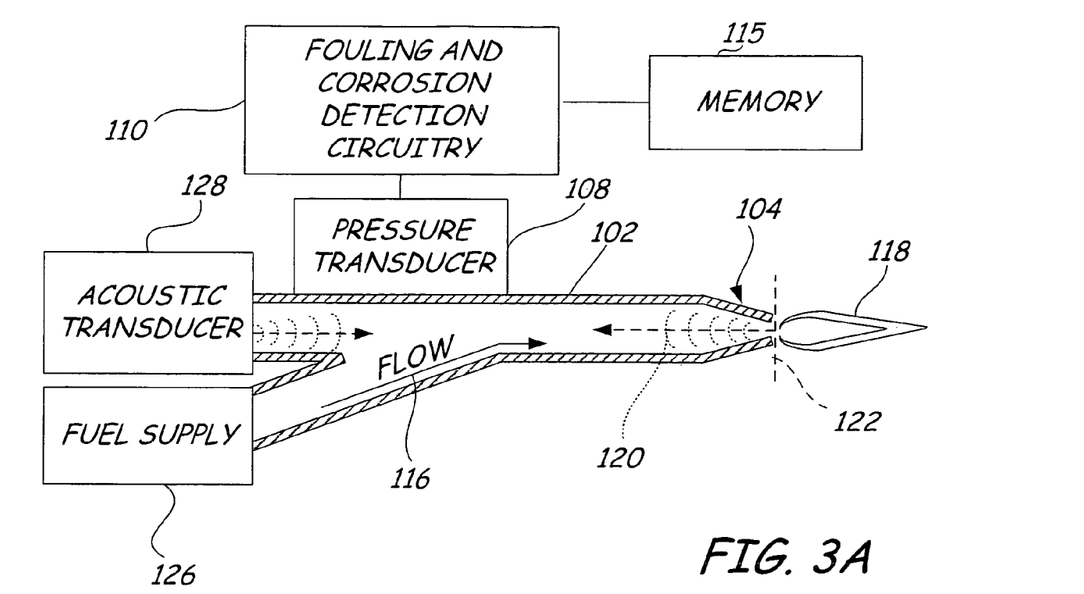
FIGS. 3A and 3B are simplified diagrams of an active acoustic burner tip fouling and corrosion detector system according to another embodiment of the present invention.
Figure 3B:
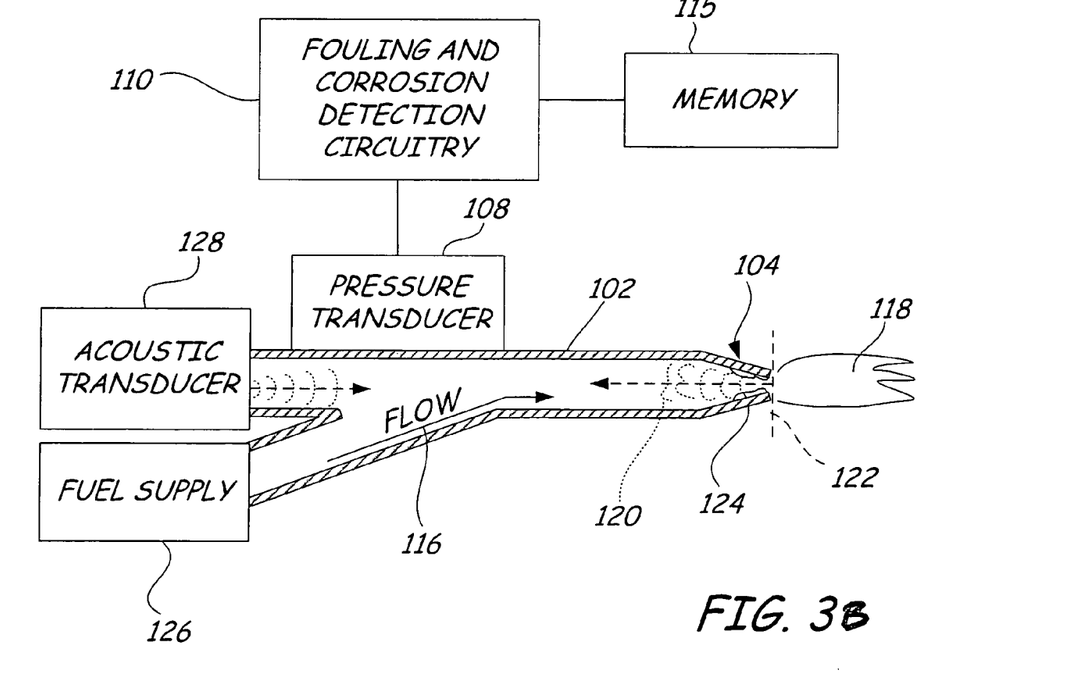

FIGS. 3A and 3B illustrate a simplified diagram of a fouling and corrosion detector according to an embodiment of the present invention for use in high noise environments. Depending on the particular installation, background noise from the process may overwhelm the ability of the transducer 108 to differentiate the burner tip signature from background noise. In such environments, it may be desirable to position an acoustic transducer 128 upstream from the burner tip 104 to direct an acoustic signal 129 at a predetermined frequency toward the burner tip 104. The fouling and corrosion detection circuitry 110 can then be configured to process the measured reflection signal 120 for a narrow band of frequencies that can be associated with the transmitted signal 129. In a preferred embodiment, acoustic transducer 128 performs both the transmitting and sensing functions, thereby simplifying the implementation. In such an embodiment, the pressure transducer 108 is simply replaced with the acoustic transducer 128.

FIG. 3B illustrates a simplified block diagram of the burner tip 104 that is partially plugged or fouled by deposits 124. Fuel supply 126 delivers the fuel to the tube 102, which in turn delivers the fuel to the burner tip 104. The transmitted signal 129 is reflected by the narrowing internal diameter of the burner tip 104 and by the deposits 124, resulting in a changed reflection signal 120, as compared with the baseline reflection signals stored in memory 115. In a preferred embodiment, the fouling corrosion and detection circuitry 110 is adapted to operate the transducer such that it sends the acoustic noise frequency. In one embodiment, the acoustic transducer 128 is adapted to send and receive the acoustic noise frequencies of interest.

In this embodiment, it may be desirable to position the transducer 108 adjacent to the acoustic transducer 128 and near the fuel flow in order to assist in measuring and canceling out the process noise from the reflected signal.

As shown, the flame 118 may be less precise or efficient in the event of a partially plugged tip 104. Instead of a tightly controlled and stable flame 118 (as shown in FIGS. 2A and 3A), the partially plugged tip 104 results in a forked flame, which if measured using an optical sensor likely would be comprised of more than one color.

In general, a key strength of this approach is that the reflected signal 120 will continuously change as the burner tip fouling increases. In addition to providing a strong predictive capability, the electronics can provide an output variable that is proportional to the degree of burner tip fouling. Moreover, by measuring a reflected signal based on the transmitted signal, the reflected signal 120 is much more dependent on the burner tip fouling than on flow velocity.

While a pressure transducer is shown, any appropriate field device capable of driving and listening for acoustic signatures may be utilized. An acoustic transducer may be utilized, for example. Moreover, other types of transmitters for measuring temperature, flow, or other process variables (PVs) may be utilized. As previously discussed, a plurality of sensors could be coupled into a single transmitter to use a common electronics. Alternatively, a fully dedicated field device can provide a low cost solution for large fired equipment because several acoustic transducers, one for each burner tip, can be brought into a common electronics.

It is important to understand that useful burner tip diagnostics should be robust for different fuel rates and resulting fuel types. If the fuel type is radically changed, as from a liquid to a gas, a new set of reference reflected signal signatures should be taken. Consequently, the local operator interface (shown as element 113 in FIG. 1) may be utilized to reset the baseline signatures as needed. Alternatively, baseline measurements may be initiated via a command issued by the control center.

Typically, fouling of the burner tip 104 causes a further narrowing of the fuel flow passageway, causing a higher frequency reflected signal or acoustic signature 120. Conversely, corrosion of the tip 104 may cause the opening to widen, thereby resulting in a lower frequency signature 120. Alternatively, corrosion or fouling may lead to uneven or odd reflections 120 (as shown in FIGS. 2B and 3B), thereby providing an early indication of possible fouling.

In general, the present invention predicts fouling and/or corrosion based on the extent of change in the reflected signal 120 as compared to the stored baseline. This allows an operator to gauge when a narrowing element within a process requires servicing. For example, when the burner tip 104 causes a change in the reflected signal 120 that exceeds a predetermined limit, the detection circuitry generates an alarm to the control center. Based on the alarm, the operator may schedule a routine service of the equipment before next use. In a batch process environment, the equipment can be serviced between batches. Such scheduled plant service shut downs are much less costly and more desirable than unplanned shutdowns due to equipment failure. Moreover, the detector takes the guess work out of determining when to service the equipment.

Figure 4A:
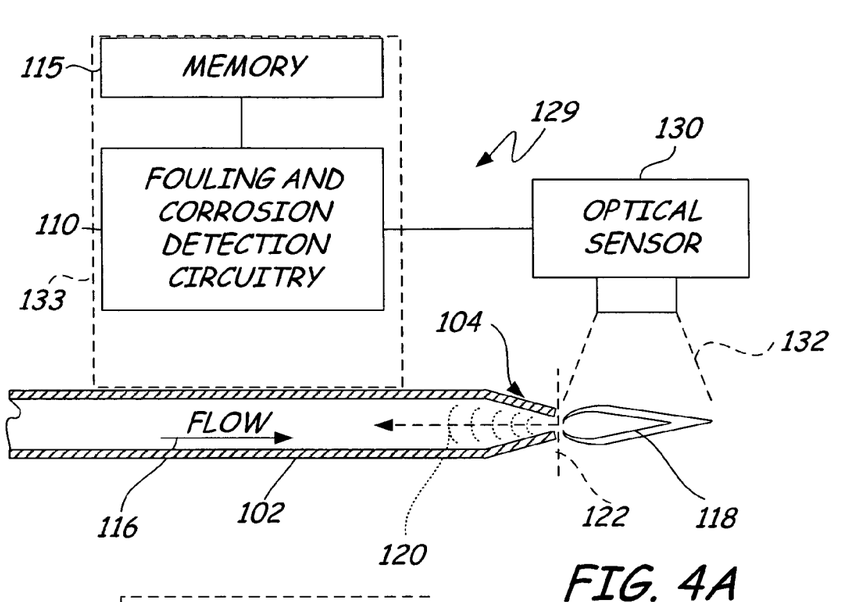
FIGS. 4A and 4B are simplified diagrams of an optical burner tip fouling and corrosion detector system according to an embodiment of the present invention.
Figure 4B:
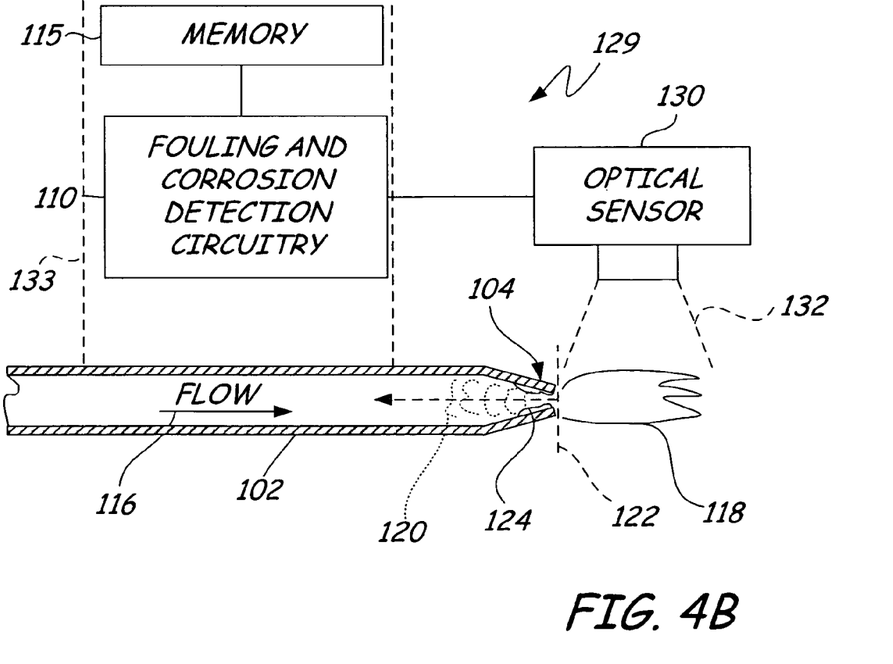

FIGS. 4A and 4B illustrate a simplified diagram of a burner tip fouling and corrosion detector adapted to capture an optical signature of a flame produced by a burner tip according to an embodiment of the present invention. As shown in FIG. 4A, the optical detector 129 includes fuel flow tube 102 with a burner tip 104, and fouling and corrosion detection circuitry 108 coupled to imaging device (optical sensor) 130. The optical sensor 130 is positioned relative to the flame 118 such that the flame 118 is within its viewing area 132. In a preferred embodiment, the imaging device 130 is positioned to the side or below the flame 118 so as to reduce the exposure of the imaging device 130 to heat produced by the flame 118. Fuel flow 116 passes through the tube 102 and out of the burner tip 104, where it is ignited to produce flame 118, which can be detected by the optical sensor 130. The optical sensor 130 relays the digitized image to the fouling and corrosion detection circuitry 110, which, in this instance, is adapted to compare the digitized flame image against a reference flame image stored in memory 115 to determine whether fouling or corrosion has occurred. For example, a flame 118 that is ignited from a gaseous fuel supply can be controlled such that the flame 118 is a constant shape and hue. However, if the tip 104 becomes fouled or plugged, the flame 118 may oscillate and change colors as impurities are consumed in the flame 118. The optical sensor 130 will detect these visual variations, and the fouling and corrosion detection circuitry 110 can identify such changes to predict fouling and/or corrosion.

FIG. 4B shows the optical detector 129 with a fouled burner tip 104, which is partially plugged by deposits 124. The fuel flow that passes through the fouled burner tip 104 is ignited to produce flame 118, which has a different shape than the flame 118 of FIG. 4A. Using the optical sensor 130, the altered shape of the flame 118 may be detected and compared against the stored baseline measurement from memory 115 to predict corrosion or fouling of the burner tip 104.

In one embodiment, the optical detector 129 consists of an imaging device coupled with electronics capable of operating the imaging device, and adapted to detect if burner tip fouling or plugging has occurred based on digitized images of the flame. Additionally, the electronics provide an output signal that either contains information about the condition of the burner tip, or outputs an alarm or warning signal that signifies that the burner tip is fouling or plugging.

The flame associated with a particular burner tip exhibits an intensity profile that is dependent on combustion conditions, the heat, color, and shape of the flame vary as the burner tip becomes fouled or plugged. The imaging device detects changes in attributes such as flame size, changes in color due to complete or incomplete combustion, flame shape, flame temperature, and the like. In normal operation, a burner tip flame profile is reasonably consistent or constant with time. However, as the tip fouls or plugs, the flame profile can take on a distinctly time-varying (oscillatory) nature (appearing to waiver, flicker or otherwise change shape and profile over time). Thus, burner tip fouling and plugging may be detected by noting a change from the reference burner tip flame profile that is measured and stored in the memory 115. If changes in the flame attributes or if the amount that the flame profile varies with time exceeds a predetermined limit, an alarm or warning is provided on the device output signal. If the burner tip 104 is completely plugged, the image of a flame may not be present at all. This allows the device to distinguish fouling or partial plugging from a fully plugged condition.

To improve sensitivity, in a preferred embodiment, an input may be provided to the diagnostic transmitter electronics from the fuel flow command signal or from a fuel flow sensor. This allows the device to re-establish reference profiles when the fuel flow through the nozzle changes. Such updating of profiles allow more sensitivity in fouling detection.

In one embodiment, a pressure transmitter 133 (shown in phantom) provides a fuel flow signal and a housing for the digital electronics 110. Alternatively, a fully dedicated device could be provided for large fired equipment because several imaging sensors, one for each burner tip, could be brought into a common electronics.

Different types of imaging technologies can be utilized with the present invention, depending on the need and on the parameter about which the designer is concerned. Color, as well as black and white imaging devices, can be used to detect differences in flame burning characteristics. Thermal imaging devices may be used to measure the optical signature, and specifically to provide a heat profile or signature associated with a burner tip. Differences in flame temperature, as well as flame characteristics could be detected. Thermal imaging or color imaging devices may also be able to detect the type of material that fouling the burner tip as the flame color and temperature may change to correspond to the chemical characteristics of the fouling material.

To determine alarm conditions, the fouling and corrosion detection circuitry may include circuitry and/or software adapted to perform pattern comparison and recognition. Various methods are known for pattern recognition in digitized images. To improve sensor accuracy and diagnostic reliability, it may be desirable to employ intelligent systems, such as a self-learning neural network or networks in conjunction with such techniques to improve the device's accuracy for a specific application while in-service. Moreover, other intelligent systems, such as fuzzy logic, artificial intelligence techniques and devices, and various time and frequency signal processing techniques, may be employed to further improve the accuracy of the device.

In general, it should be understood by workers skilled in the art that an alarm may be an electronic signal, which is transmitted, for example, to a control center. Alternatively, the alarm may be a visual signal at the apparatus, such as a lit LED, a flashing display, and the like.

While the above-described embodiments have largely focused on fouling of the burner tip, corrosion may also be detected using the same technique. For example, an acoustic detector, such as that shown in FIGS. 2A-3B, would likely detect a decreasing frequency (and possibly some attenuation) in the reflected acoustic signature 120 of the burner tip 104 if the burner tip 104 erodes or becomes corroded, as compared with a reference signature stored in memory 115.

As the burner tip 104 becomes corroded, the flame 118 itself changes as well. For example, corrosion of the burner tip 104 may impact the fuel flow and thus the fuel/air mixture resulting in changes in heat signature and flame coloration. Additionally, corrosion may effect the shape of the burner tip 104, resulting in changes in shape and in "steadiness" or oscillation of the flame 118. Such changes are detectable by an optical detector 130 as discussed above.

The burner tip fouling and corrosion detection system described above provides a number of advantages over prior art systems. All three embodiments use a burner tip signature to provide a sensitive, predictive method of determining burner tip fouling. Moreover, all three embodiments are simple to mount and implement, and the detection means may be integral to the transmitter if desired. In the optical detection system, the imaging device may be mounted in any position having a good view of the combustion flame to be monitored. In a preferred embodiment, the imaging device is positioned away from the heat, such as below or to the side of the flame.

None of the three embodiments require a fuel flow rate measurement to provide information on fouling or plugging of the burner tip; however, in all three cases, such data may be used to improve the detector's sensitivity. Moreover, none of the three embodiments loads the DCS beyond a transmitter PV or an alarm input, in the preferred embodiment.

Both the driven acoustic detector and the imaging detector provide a way of detecting increasing fouling, allowing the diagnostic device to output a signal that is responsive to the amount of fouling. The driven acoustic detector also readily handles variations in fuel flow.

For most applications, both acoustic sensors can operate on a 4-20 mA loop power supply, and both can readily distinguish between a fuel off condition and a plugging event. Finally, the passive acoustic detector can provide a fuel pressure PV as a side benefit.

Finally, it should be noted that the present invention has been described with respect to burner tip output signatures and flame output signatures; however, the present invention is applicable to other flow-restrictive or flow-obstructive devices.

Figure 5A:
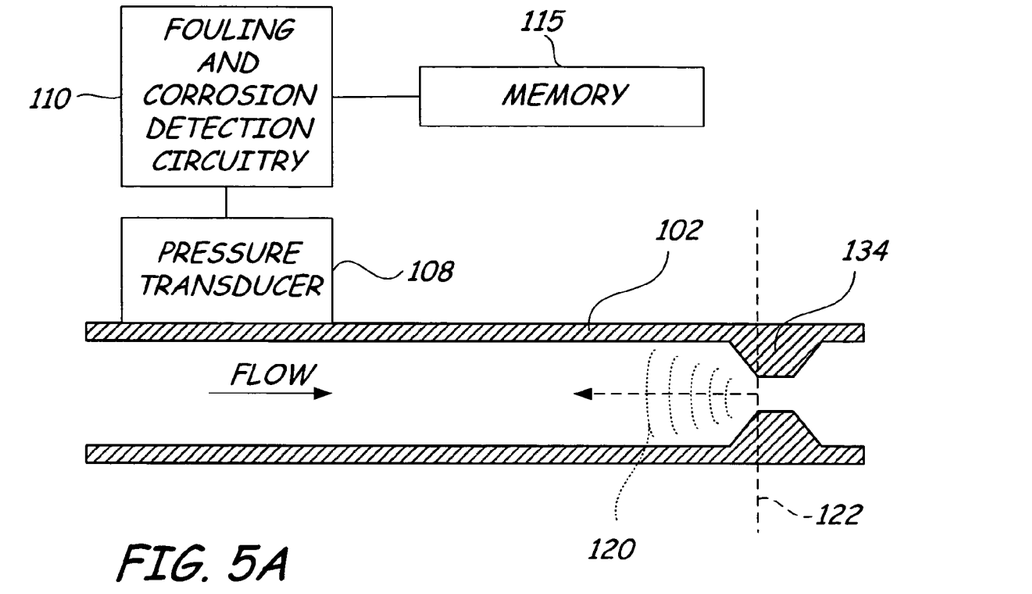
FIGS. 5A and 5B are simplified diagrams of a passive acoustic fouling and corrosion detector system for use with any flow restrictive element according to an embodiment of the present invention.
Figure 5B:
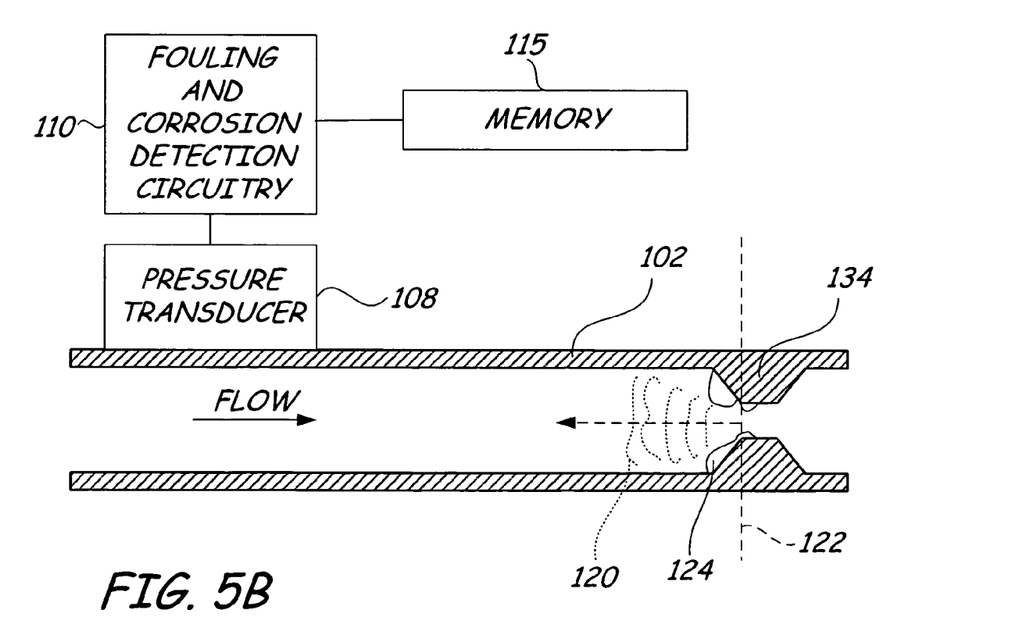

FIGS. 5A and 5B illustrate a simplified diagram of a process with a flow-restrictive element 134 disposed within the pipe or tube 102. For simplicity sake, the embodiment is similar to that of the passive scheme of FIG. 2A; however, an acoustic transducer (such as that shown in FIGS. 3A and 3B) may be used to transmit a signal toward the narrowing element. In alternative embodiment, the acoustic transducer may be positioned on the pipe 102 on an opposing side of the flow restriction relative to the pressure transducer 108, such that the transmitted acoustic signal would be reflected and a portion of the signal would pass through the flow restriction to be measured. The change in the received signal relative to the baseline would be indicative of fouling within the flow restrictive element 134.

Nevertheless, as shown, the flow of fluid is forced through the restriction 134, thereby generating a reflected noise signal 120. The reflected noise signal can be detected by the pressure transducer 108 and compared by the fouling and corrosion detection circuitry 110 to baseline signals stored in memory 115. If differences between the measured signal 120 and the stored signals exceed a predetermined limit, an alarm signal can be generated to the control center indicating that the restriction element 134 may require service soon.

In general, plugging or corrosion may be detected by comparing a reflected acoustic signature of any partial obstruction or flow restriction of a fluid flow against a reference signature. The flow restriction 134 may be a Venturi tube, an orifice plate, a shedding bar, a valve, a nozzle, and the like. As such devices become corroded or fouled, the reflected acoustic signature changes. Moreover, the optical detector may be applied to any type of flow output that can be detected optically, including high temperature flows, and the like. In such an embodiment, an infrared detector, for example, can be used to monitor changes in the temperature profile of the fluid flow.

The present invention also provides an advantage in that it is possible to detect developing problems in an industrial process based on significant changes in background noise, independent of the acoustic signature used to predict fouling and corrosion. For example, in moving equipment, as bearings begin to fail, the equipment generates increasing noise output. This change in noise output will alter the background noise of the detected signal, and significant changes can be analyzed to predict potential service needs of other adjacent equipment, before catastrophic failure.

Although the present invention has been described with reference to preferred embodiments, workers skilled in the art will recognize that changes may be made in form and detail without departing from the spirit and scope of the invention.

What is claimed is:

1. A system for predicting fouling and corrosion of a combustion system in an industrial process comprising:
   a pipe in the industrial process containing a fuel;
   a restrictive element coupled to the pipe and which leads to a combustion chamber of the combustion system which generates a back pressure in the pipe; and
   a fouling and corrosion detector coupled to the pipe and adapted to detect a characteristic signature having a time varying component of the fuel flowing through the restrictive element and into the combustion chamber of the combustion system, the characteristic signature reflected from the restrictive element;
   wherein the characteristic signature comprises a reflected acoustic signal; and
   wherein the fouling and corrosion detector comprises:
      an acoustic transducer coupled to the pipe and adapted to detect acoustic signals in the fuel in the pipe;
      a memory configured to store baseline characteristic acoustic signatures, and wherein the fouling and corrosion detector is configured to store a plurality of baseline characteristic acoustic signatures during normal operation of the restrictive element, the plurality of baseline characteristic acoustic signatures measured at different back pressures in the pipe; and
      fouling and corrosion detection circuitry coupled to the acoustic transducer and to the memory and adapted to compare the characteristic signature detected by the acoustic transducer of a current back pressure against one of the stored plurality of baseline characteristic acoustic signatures obtained at a back pressure and responsively identify fouling or corrosion of the restrictive element based upon the comparison.

2. The system of claim 1 wherein the restrictive element comprises a burner tip within a heat delivery system of the industrial process.

3. The system of claim 1 wherein the fouling and corrosion detector is adapted to detect changes in background noise indicative of problems within the industrial process independent of fouling or corrosion.

4. The system of claim 1 wherein the fouling and corrosion detector comprises: intelligent systems adapted to analyze the characteristic signature.

5. The system of claim 1 wherein detector is adapted to detect the characteristic signature using wavelet technology.

6. The system of claim 1 further comprising:
a local operator interface adapted to allow a user to set a baseline characteristic acoustic signature.

7. A system for monitoring fouling and corrosion of fired equipment within an industrial process, the system comprising:
a pipe in the industrial process containing a fuel;
a burner tip in a combustion chamber of the fired equipment and coupled to the pipe and adapted to deliver the fuel to the combustion chamber of the fired equipment, the burner tip defining a flow restriction at one end of the pipe and creating a back pressure in the pipe;
a transducer coupled to the pipe and adapted to detect an acoustic signature having a time varying component which is reflected from the burner tip;
wherein the acoustic signature comprises a detectable acoustic signal caused by the fuel flowing through the burner tip; and
circuitry adapted to store a plurality of baseline characteristic acoustic signatures during normal operation of the burner tip, the plurality of baseline characteristic acoustic signatures measured at different back pressures in the pipe and process the detected acoustic signature at a current back pressure against one of the plurality of stored baseline characteristic acoustic signatures obtained at a back pressure and to generate an alarm signal if the detected acoustic signature varies sufficiently from the one of the stored plurality of baseline characteristic acoustic signatures;
the acoustic transducer adapted to direct an acoustic signal toward the burner tip.

8. The system of claim 7 wherein the reflection varies as the burner tip becomes fouled or corroded.

9. The system of claim 7 and further comprising:
intelligent systems coupled to the circuitry and adapted to analyze the detected acoustic signature to predict fouling and/or corrosion of the burner tip.

* * * * *